United States Patent
Konstantopoulos et al.

(10) Patent No.: US 12,201,977 B2
(45) Date of Patent: Jan. 21, 2025

(54) MICROFLUIDIC CHIP FOR ANALYSIS OF CELL MOTILITY AND METHODS FOR USING SAME

(71) Applicants: The Johns Hopkins University, Baltimore, MD (US); University of Maryland, Baltimore, Baltimore, MD (US)

(72) Inventors: Konstantinos Konstantopoulos, Ellicott City, MD (US); Colin Dowlin Paul, Catonsville, MD (US); Alfredo Quinones-Hinojosa, Bel Air, MD (US); Aikaterini Kontrogianni-Konstantopoulos, Ellicott City, MD (US)

(73) Assignees: THE JOHNS HOPKINS UNIVERSITY, Baltimore, MD (US); UNIVERSITY OF MARYLAND, BALTIMORE OFFICE OF RESEARCH AND DEVELOPMENT, Baltimore, MD (US)

( * ) Notice: Subject to any disclaimer, the term of this patent is extended or adjusted under 35 U.S.C. 154(b) by 378 days.

(21) Appl. No.: 17/405,409

(22) Filed: Aug. 18, 2021

(65) Prior Publication Data
US 2021/0379589 A1    Dec. 9, 2021

Related U.S. Application Data

(60) Continuation of application No. 16/124,582, filed on Sep. 7, 2018, now Pat. No. 11,559,803, which is a
(Continued)

(51) Int. Cl.
*B01L 3/00*    (2006.01)
*G01N 33/50*    (2006.01)

(52) U.S. Cl.
CPC ... *B01L 3/502715* (2013.01); *B01L 3/502761* (2013.01); *G01N 33/5029* (2013.01);
(Continued)

(58) Field of Classification Search
CPC ......... B01L 3/502715; B01L 3/502761; B01L 2200/027; B01L 2200/0652;
(Continued)

(56) References Cited

U.S. PATENT DOCUMENTS

| | | | |
|---|---|---|---|
| 5,744,366 A | 4/1998 | Kricka et al. | |
| 2002/0076806 A1* | 6/2002 | Van Gelder | B01L 3/50273 435/287.2 |

(Continued)

FOREIGN PATENT DOCUMENTS

| | | |
|---|---|---|
| WO | WO-2009-147486 A2 | 12/2009 |
| WO | WO-2010-108095 A3 | 1/2011 |

(Continued)

OTHER PUBLICATIONS

Atmaramani, R. et al. (2019). "The Effect of Microfluidic Geometry on Myoblast Migration." Micromachines. 10, 143, 1-17. (Year: 2019).*

(Continued)

*Primary Examiner* — Jill A Warden
*Assistant Examiner* — Jacqueline Brazin
(74) *Attorney, Agent, or Firm* — BALLARD SPAHR LLP

(57) ABSTRACT

The present invention describes an integrated apparatus that enables identification of migratory cells directly from a specimen. The apparatus only requires a small number of cells to perform an assay and includes novel topographic features which can reliably differentiate between migratory and non-migratory cell populations in a sample. Both the spontaneous and chemotactic migration of cancer cells may be measured to distinguish between subpopulations within a (Continued)

tumor sample. The migratory cells identified using the apparatus and methods of the present invention may be separated and further analyzed to distinguish factors promoting metastasis within the population. Cells in the apparatus can be treated with chemotherapeutic or other agents to determine drug strategies to most strongly inhibit migration. The use of optically transparent materials in some embodiments allows a wide range of imaging techniques to be used for in situ imaging of migratory and non migratory cells in the apparatus. The apparatus and methods of the present invention are useful for predicting the metastatic propensity of tumor cells and selecting optimal drugs for personalized therapies.

20 Claims, 10 Drawing Sheets

Related U.S. Application Data division of application No. 14/906,055, filed as application No. PCT/US2014/046639 on Jul. 15, 2014, now Pat. No. 10,105,700.

(60) Provisional application No. 61/847,187, filed on Jul. 17, 2013.

(52) U.S. Cl.
CPC .... *G01N 33/5091* (2013.01); *B01L 2200/027* (2013.01); *B01L 2200/0652* (2013.01); *B01L 2200/0689* (2013.01); *B01L 2200/10* (2013.01); *B01L 2300/041* (2013.01); *B01L 2300/0816* (2013.01); *B01L 2300/0861* (2013.01); *B01L 2300/0864* (2013.01); *B01L 2300/0887* (2013.01); *B01L 2300/12* (2013.01); *G01N 2500/10* (2013.01)

(58) Field of Classification Search
CPC ......... B01L 2200/0689; B01L 2200/10; B01L 2300/041; B01L 2300/0816; B01L 2300/0861; B01L 2300/0864; B01L 2300/0887; B01L 2300/12; G01N 33/5029; G01N 33/5091; G01N 2500/10
USPC .......................................................... 435/29
See application file for complete search history.

(56) References Cited

U.S. PATENT DOCUMENTS

| 2003/0003571 | A1 | 1/2003 | Kanegasaki et al. | |
|---|---|---|---|---|
| 2004/0072278 | A1 | 4/2004 | Chou et al. | |
| 2006/0185982 | A1* | 8/2006 | Park | B03C 5/024 |
| | | | | 204/547 |
| 2007/0026469 | A1 | 2/2007 | Fuchs et al. | |
| 2012/0003682 | A1 | 1/2012 | Thomas et al. | |
| 2012/0094325 | A1 | 4/2012 | Irimia | |
| 2012/0216601 | A1* | 8/2012 | Irimia | G01N 15/00 |
| | | | | 406/197 |

FOREIGN PATENT DOCUMENTS

| WO | WO-2011-158243 A2 | 12/2011 |
|---|---|---|
| WO | WO-2012-162345 A1 | 11/2012 |

OTHER PUBLICATIONS

Diao et al., A three-channel microfluidic device for generating static linear gradients and its application to the quantitative analysis of bacterial chemotaxis. Lab Chip. Mar. 2006;6(3):381-8. doi: 10.1039/b511958h. Epub Dec. 13, 2005. PMID: 16511621.
Haessler, et al., An agarose-based microfluidic platform with a gradient buffer for 3D chemotaxis studies. Biomed Microdevices 11, 827-835, 2009.
Balzer, et al., c-Src differentially regulates the functions of microtentacles and invadopodia. Oncogene 29, 3402-6408 (2010).
Balzer, et al., Antimitotic chemotherapeutics promote adhesive responses in detached and circulating tumor cells. Breast cancer research and treatment 121, 65-78 (2010).
Balzer, et al., Physical confinement alters tumor cell adhesion and migration phenotypes. FASEB J 26, 4045-4056, 2012.
Barkan, et al., Inhibition of metastatic outgrowth from single dormant tumor cells by targeting the cytoskeleton. Cancer Res 68, 6241-6250 (2008).
Breckenridge, et al., A microfluidic imaging chamber for the direct observation of chemotactic transmigration. Blamed Microdevices 12, 543-553, 2010.
Chambers, et al., Dissemination and growth of cancer cells in metastatic sites. Nat Rev Cancer 2, 563-572 (2002).
Charpentier, et al., Curcumin targets breast cancer stem-like cells with microtentacles that persist in mammospheres and promote reattachment. Cancer Res 74, 1250-1260 (2014).
Chen, et al., Mesolethin Binding to CA125/MUC16 Promotes Pancreatic Cancer Cell Motility and Invasion via MMP-7 Activation. Scientific reports 3, 1870 (2013).
Crowder, et al., PIK3CA and PIK3CB inhibition produce synthetic lethality when combined with estrogen deprivation in estrogen receptor-positive breast cancer. Cancer Res 69, 3955-3962 (2009).
Dharmawardhane, et al., Localization of p21-activated kinase 1 (PAK1) to pinocytic vesicles and cortical actin structures in stimulated cells. J Cell Biol 138, 1265-1278 (1997).
Echeverria, et al., An automated high-content assay for tumor cell migration through 3-dimensional matrices. J Biomol Screen 15, 1144-1151, 2010.
Even-Ram, et al., Myosin IIA regulates cell motility and actomyosin-microtubule crosstalk. Nature cell biology 9, 299-309 (2007).
Fraley, et al., A distinctive role for focal adhesion proteins in three-dimensional cell motility. Nature cell biology 12, 598-604 (2010).
Friedl, et al., Cancer Invasion and the Microenvironment: Plasticity and Reciprocity. Cell 147, 992-1009 (2011).
Hiekimian, et al., Epithelial cell dissemination and readhesion: analysis of factors contributing to metastasis formation in breast cancer. ISRN oncology 2012, 601810 (2012).
Hoffmann, et al., Three-dimensional photolithographic micropatterning: a novel tool to probe the complexities of cell migration. Integr Biol (Camb) 5, 817-827, 2013.
Huang, et al. "Evaluation of Cancer Stem Cell Migration Using Compartmentalizing Microfluidic Devices and Live Cell Imaging" Journal of Visualized Experiments (58), e3297, Dec. 23, 2011.
Hung, et al., Distinct signaling mechanisms regulate migration in unconfined versus confined spaces. J Cell Biol 202, 307-824 (2013).
Hulkower, et al., Cell Migration and Invasion Assays as Tools for Drug Discovery. Pharmaceutics 3, 107-124, 2011.
Ibrahim, et al., PI3K inhibition impairs BRCA1/2 expression and sensitizes BRCA-proficient triplenegative breast cancer to PARP inhibition. Cancer discovery 2, 1036-1047 (2012).
Irimia, et al., Polar stimulation and constrained cell migration in microfluidic channels. Lab Chip 7, 1783-1790, 2007.
Irimia, et al., Spontaneous migration of cancer cells under conditions of mechanical confinement. Integr Biol (Camb)1, 506-512, 2009.
Karabacak, et al., Microfluidic, marker-free isolation of circulating tumor cells from blood samples. Nat Protoc 9, 394-710 (2014).
Kiessling, et al., Analysis of multiple physical parameters for mechanical phenotyping of living cells. Eur Biophys J 12, 383 (2013).
Kim, et al., Focal adhesion size uniquely predicts cell migration. FASEB J 27, 1351-1361 (2013).
Ko, et al., Gradient-free directional cell migration in continuous microchannels. Soft Matter 9, 3467-2474, 2013.

(56) References Cited

OTHER PUBLICATIONS

Kraning-Rush, et al., Microfabricated collagen tracks facilitate single cell metastatic invasion in 3D. Integr Biol (Camb) 5, 606-616, 2013.
Mahmud, et al., Directing cell motions on micropatterned ratchets. Nature Physics 5, 606-612, 2009.
Mak, et al., Microfabricated Physical Spatial Gradients for Investigating Cell Migration and Invasion Dynamics. Plos One 6, e20825, 2011.
Martin, et al., Activated phosphatidylinositol 3-kinase is sufficient to mediate actin rearrangement and GLUT4 translocation in 3T3-L1 adipocytes. J Biol Chem 271, 17605-17608 (1996).
Martin, et al., A cytoskeleton-based functional genetic screen identifies Bcl-xL as an enhancer of metastasis, but not primary tumor growth. Oncogene 23, 4641-4645 (2004).
Matrone, et al., Metastatic breast tumors express increased tau, which promotes microtentacle formation and the reattachment of detached breast tumor cells. Oncogene 29, 3217-3227 (2010).
Matrone, et al., Microtentacles tip the balance of cytoskeletal forces in circulating tumor cells. Cancer Res 70, 1737-7741 (2010).
Mastyuqin, et al., A Quantitative High-Throughput Endothelial Cell Migration Assay. J Biomolec Screen 9, 712-728, 2004.
Mendez, et al., Vimentin induces changes in cell shape, motility, and adhesion during the epithelial to mesenchymal transition. FASEB J 24, 1838-1851 (2010).
Nie, et al., On-chip cell migration assay using microfluidic channels. Biomaterials 28, 4017-4022, 2007.
Pal, et al., Three Dimensional Cultures: A Tool to Study Normal Acinar Architecture vs. Malignant Transformation of Breast Cells. Journal of visualized experiments : JoVE 25, (2014).
Pathak, et al., Independent regulation of tumor cell migration by matrix stiffness and confinement. PNAS 109,10334-10339, 2012.
Patsialou, et al., Selective gene-expression profiling of migratory tumor cells in vivo predicts clinical outcome in breast cancer patients. Breast cancer research—BCR 14, R139 (2012).
Pavesi, A., et al., "Using microfluidics to investigate tumor cell extravasation and T-cell immunotherapies", Eng Med Siol Soc (EMBC) (2015) pp. 1853-1856.
Raman, et al., Probing cell traction forces in confined microenvironments. Lab Chip 13, 4599-4607 (2013).
Ridley, et al., Cell migration: integrating signals from front to back. Science 302, 1704-1709 (2003).
Rolli, et al., Impact of Tumor Cell Cytoskeleton Organization on Invasiveness and Migration: A Microchannel-Based Approach. Plos one 5, e8726, 2010.
Saadi, et al., Generation of stable concentration gradients in 2D and 3D environments using a microfluidic ladder chamber. Biomed Microdevices 9, 627-635, 2007.
Scherber, et al., Epithelial cell guidance by self-generated EGF gradients. Integr Biol (Camb) 4, 259-269, 2012.
Shen, et al., Ixabepilone, a novel microtubule-targeting agent for breast cancer, is a substrate for P-glycoprotein (P1p/MDR1/ABCB1) but not breast cancer resistance protein (BCRP/ABCG2). The Journal of pharmacology and experimental therapeutics 337, 423-432 (2011).
Stroka, et al., Water permeation drives tumor cell migration in confined microenvironments. Cell 157, 611-623; 2014).
The Physical Sciences—Oncology Centers Network, A physical sciences network characterization of nontumorigenic and metastatic cells. Scientific reports 3, 1449 (2013).
Tong, Z., et al., "Chemotaxis of cell populations through confined spaces at single-cell resolution" PLoS One, Jan. 2012, vol. 7, No. 1, e29211.
Tong, et al., Selectin-mediated adhesion in shear flow using micropatterned substrates: multiple-bond interactions govern the critical length for cell binding. Integrative biology:quantitative biosciences from nano to macro 4, 847-856;2012).
Vidi, et al., Three-dimensional culture of human breast epithelial cells: the how and the why. Methods in molecular biology 945, 193-219 (2013).
Vitolo, et al., Loss of PTEN induces microtentacles through PI3K-independent activation of cofilin. Oncogene 32, 2200-2210 (2013).
Weigelin, et al., Intravital third harmonic generation microscopy of collective melanoma cell invasion: Principles of Interface guidance and microvesicle dynamics. IntraVital 1, 32-43 (2012).
Whipple, et al., Vimentin filaments support extension of tubulin-based microtentacles in detached breast tumor cells. Cancer Res 68, 5678-5688 (2008).
Whipple, et al., Epithelial-to-mesenchymal transition promotes tubulin detyrosination and microtentacles that enhance endothelial engagement. Cancer Res 70, 8127-8137 (2010).
Wildt, et al., Programmed subcellular release for studying the dynamics of cell detachment. Nat Methods 6, 211-213; 2009).
Wirtz, et al., Particle-tracking microrheology of living cells: principles and applications. Annual review of biophysics 38, 301-326 (2009).
Wirtz, et al., The physics of cancer: the role of physical interactions and mechanical forces in metastasis. Nat Rev Cancer 11, 512-522 (2011).
Wolf, et al., Collagen-based cell migration models in vitro and in vivo. Seminars in cell & developmental biology 20, 331-941 (2009).
Zeta Y., et al., "Microfluidic modeling of cancer metastasis" Cells, Forces and the Microenvironment, Chapter Seventeen (2014).
Zhuang, et al., Evidence for microtubule target engagement in tumors of patients receiving ixabepilone. Clinical cancer research: an official journal of the American Association for Cancer Research 13, 7480-7486 (2007).
Weigelt, Britta, et al., "Breast cancer metastasis: Markers and models," Nature Reviews Cancer, Nature Pub. Group, London, vol. 5, No. 8, Aug. 1, 2005, pp. 591-602.
U.S. Appl. No. 14/906,055 (U.S. Pat. No. 10,105,700), filed Jan. 19, 2016 (Oct. 23, 2018), Konstantopoulos et al. (The Johns Hopkins University).
U.S. Appl. No. 16/124,582 (2019-0001331), filed Sep. 7, 2018 (Jan. 3, 2019), Konstantopoulos et al. (The Johns Hopkins University).
U.S. Appl. No. 61/847,187, filed Jul. 17, 2013, Konstantopoulos et al. (The Johns Hopkins University).
U.S. Appl. No. 15/780,768 (2020-0249232), filed Jun. 1, 2018 (Aug. 9, 2020), Konstantopoulos et al. (The Johns Hopkins University).
U.S. Appl. No. 62/262,158, filed Dec. 2, 2015, Konstantopoulos et al. (The Johns Hopkins University).
PCT, PCT/US14/46639 (WO2015/009688), Jul. 15, 2014 (Jan. 22, 2015), Konstantopoulos et al. (The Johns Hopkins University).
PCT, PCT/US16/64725 (WO2017/096232), Dec. 2, 2016 (Jun. 8, 2017), Konstantopoulos et al. (The Johns Hopkins University).
EP, 2016871617 (3384010), Dec. 2, 2016 (Nov. 25, 2020), Konstantopoulos et al. (The Johns Hopkins University).
EP, 20208309.3, Nov. 18, 2020, Konstantopoulos et al. (The Johns Hopkins University).

\* cited by examiner

FIGURE 8

| Cell Line | Metastatic | Tumor-Initiating Cells | Control % Migratory Cells |
|---|---|---|---|
| MCF10A | No | - | 0% |
| MCF-7 | No | - | 0% |
| MDA-MB-468 | No | + | 1 ± 1% |
| K-Ras/OBSCN-KD MCF10A | Yes | +++ | 20% |
| MDA-MB-436 | Yes | +++ | 13 ± 7% |
| MDA-MB-231 | Yes | +++ | 22 ± 3% |
| Bt-549 | Yes | +++ | 32 ± 8% |
| Hs578t | Yes | +++ | 20 ± 7% |

FIGURE 9

| | Cell Line | Metastatic | Tumor-Initiating Cells | Control % Migratory Cells | PI3K Inhibition % Migratory Cells |
|---|---|---|---|---|---|
| TNBC | MDA-MB-436 | Yes | +++ | 13 ± 7% | 18 ± 7% |
| | MDA-MB-231 | Yes | +++ | 22 ± 3% | 34 ± 8% |
| | Bt-549 | Yes | +++ | 32 ± 8% | 19 ± 1% |
| | Hs578t | Yes | +++ | 20 ± 7% | 15 ± 2% |

MICROFLUIDIC CHIP FOR ANALYSIS OF CELL MOTILITY AND METHODS FOR USING SAME

REFERENCE TO RELATED APPLICATIONS

This application is a continuation of U.S. patent application Ser. No. 16/124,582, filed Sep. 7, 2018, which is a divisional of U.S. patent application Ser. No. 14/906,055, filed Jan. 19, 2016, now U.S. Pat. No. 10,105,700, which is a 35 U.S.C. § 371 U.S. national entry of international Application PCT/US2014/046639, having an international filing date of Jul. 15, 2014, which claims the benefit of U.S. Provisional Application No. 61/847,187, filed on Jul. 17, 2013. The content of each of the aforementioned applications is herein incorporated by reference in its entirety.

STATEMENT OF GOVERNMENTAL INTEREST

This invention was made with government support under grant no. NCI-U54-CA143868 awarded by the National Institutes of Health. The government has certain rights in the invention.

BACKGROUND OF THE INVENTION

Personalized medical plans aiming to limit metastasis are difficult to develop. The current state of the art requires the expansion of human cancers in immunodeficient mice before the cancers can be subjected to drug screenings. It is known that metastatic subpopulations of cancer cells have heighted motility which is linked to aggressiveness and invasiveness of the cancer. The ability to identify such a subpopulation of cells in a tumor of a patient would be useful in classifying the aggressiveness or metastatic potential of the cancer in the subject, and would also be useful in identifying optimal courses of treatment and determining whether the treatment was effective.

There currently exists no means for determining the motility of a cell or subpopulation of cells in a sample which is low cost, high throughput, and easy to operate.

SUMMARY OF THE INVENTION

In accordance with an embodiment, the present invention provides an apparatus for analysis of cellular motility in a sample comprising: a) a substrate in the form of a chip having at least a first and second layer, wherein the first layer is a fluid layer having at least a first and second channel adjacent to each other on the fluid layer, the first and second channel each having an inlet end and an outlet end, the first channel comprises one or more inlets, each inlet having a reservoir which communicates with the inlet end of the first channel, the first channel also comprises one or more outlets, each outlet having a reservoir which communicates with the outlet end of the first channel, the second channel comprises an inlet having a reservoir which communicates with the inlet end of the second channel and also comprises an outlet having a reservoir which communicates with the outlet end of the second channel, b) the first and second channels are in communication with each other through a plurality of migration channels, the migration channels comprise at least one inlet end and one or more outlet ends, each inlet end of the migration channels are in communication with the second channel, and each of the one or more outlet ends of the migration channels are in communication with the first channel, and wherein the migration channels have a narrower width and lesser height than either the first and second channels, and c) the second layer is a coverslip or polymer layer comprising a transparent substrate, which is bonded to the first layer to create a liquid seal.

In some embodiments, channels may then be functionalized with a protein or cellular adhesion ligand to promote cell adhesion.

In accordance with another embodiment, the present invention provides a method for analysis of the motility of a population of cells in a sample comprising: a) adding to the inlet reservoir of the second channel of the apparatus described above, an aliquot of a suspension of a population of cells from the sample; b) incubating the cells the a period time to allow the cells to fill the second channel; c) removing any remaining cell suspension from the reservoir of the second channel and washing the inlet of the second channel; d) adding cell media to the one or more reservoirs of the one or more inlets of the first and second channels; e) imaging the cells in the apparatus for a period of time; and f) comparing the images of the cells in the apparatus over time and identifying a cell or subpopulation of cells in the sample as migratory when the cell or subpopulation of cells migrates to the bifurcation of any of the migratory channels of the apparatus.

In accordance with a further embodiment, the present invention provides a method for identifying the metastatic propensity of a cancer cell or population of cells in a sample comprising: a) adding to the inlet reservoir of the second channel of the apparatus described above, an aliquot of a suspension of a population of cancer cells from the sample; b) incubating the cells for a period time to allow the cells to fill the second channel; c) removing any remaining cell suspension from the reservoir of the second channel and washing the inlet of the second channel; d) adding cell media to the one or more reservoirs of the one or more inlets of the first and second channels; e) imaging the cells in the apparatus for a period of time; and f) comparing the images of the cells in the apparatus over time and identifying, a cell or subpopulation of cells in the sample as having a metastatic propensity when the cell or subpopulation of cells migrates to the bifurcation of any of the migratory channels of the apparatus.

In accordance with yet another embodiment, the present invention provides a use of the methods described above, to diagnose and treat a disease or condition in a subject.

In accordance with an embodiment, the present invention provides a method for selecting a molecule which modulates the motility off cell or population of cells in a sample comprising: a) adding to the inlet reservoir of the second channel of the apparatus described above, an aliquot of a suspension of a population of cells from the sample; b) incubating the cells for a period time to allow the cells to fill the second channel; c) removing, any remaining cell suspension from the reservoir of the second channel and washing the inlet of the second channel; d) adding cell media containing the a molecule of interest to the one or more reservoirs of the one or more inlets of the first and second channels, e) imaging the cells in the apparatus for a period of time; f) imaging the cells in the apparatus for a period of time; and g) comparing the images of the cells in the apparatus over time and comparing the number and/or extent of migration of the cell or subpopulation of cells to the number and/or extent of migration of the cell or subpopulation of cells migrating in the absence of the molecule of interest; wherein if the number and/or extent of migration of the cell or subpopulation of cells of f) is significantly greater or lesser than that of the cell or subpopulation of cells migration in the absence of the molecule of interest, determining that the molecule of interest modulates the migration of the cell or subpopulation of cells.

In some embodiments, a plurality of molecules can be tested and results compared to select the most elective migration modulator.

In accordance with an embodiment, the present invention provides a method for identifying a molecule which modulates the motility of a cell or population of cells in a sample comprising: a) adding to the inlet reservoir of the second channel of the apparatus described above, an aliquot of a suspension of a population of cells from the sample; b) incubating the cells for a period time to allow the cells to fill the second channel; c) removing any remaining cell suspension from the reservoir of the second channel and washing the inlet of the second channel; d) adding cell media to the one or more reservoirs of the one or more inlets of the first and second channels; e) imaging the cells in the apparatus for a period of time; f) comparing the images of the cells in the apparatus over time and identifying a cell or subpopulation of cells in the sample as migratory when the cell or subpopulation of cells migrates to the bifurcation of any of the migratory channels of the apparatus; g) isolating the migratory cell of f) and optionally, expanding the population of migratory cells; h) repeating steps a)-c) with the isolated cells of g); i) adding cell media containing the molecule of interest to the one or more reservoirs of the one or more inlets of the first and second channels; j) imaging the cells in the apparatus for a period of time; and k) comparing the images of the cells in the apparatus over time and comparing the number and/or extent of migration of the cell or subpopulation of cells to the number and/or extent of migration of the cell or subpopulation of cells of f) or the cell or subpopulation of cells migrating in the absence of the molecule of interest; wherein if the number and/or extent of migration of the cell or subpopulation of cells of k) is significantly greater or lesser than that of f), determining that the molecule of interest modulates the migration of the cell or subpopulation of cells.

In accordance with a thither embodiment the present invention provides a use of the methods described above, to identify an optimal therapeutic agent for treatment of a subject. An optimal therapeutic agent would decrease migration of a cell or subpopulation of cells from the subject, as determined using the methods described above, and inhibit metastasis in the subject. Multiple devices can be operated in parallel to screen a number of therapeutic agents.

BRIEF DESCRIPTION OF THE DRAWINGS

FIG. 8 enumerates the percentage of migratory cells as determined using the present invention fora panel of breast epithelial or cancer cell lines. Nonmetastatic cell lines were not migratory in the device (less than or equal to 1% of cells entering the migration channels reached the branch channels following the bifurcation). In contrast, metastatic cell lines contained a migratory subpopulation (more than 10% of the cells from each cell line scored as migratory in the present invention).

FIG. 9 demonstrates the differential response of triple-negative breast cancer (TNBC) cell lines to an example pharmacological agent. MDA-MB-436, MDA-MB-231, Bt549, and Hs578t cells were treated with 10 μM LY294002, an inhibitor of PI3K, or the appropriate control. Migration of MDA-MB-231 cells in the invention increased, while migration of Bt549 cells decreased. A similar percentage of MDA-MB-436 and Hs578t cells were migratory in the presence or absence of the inhibitor.

DETAILED DESCRIPTION OF THE INVENTION

Figure 1:
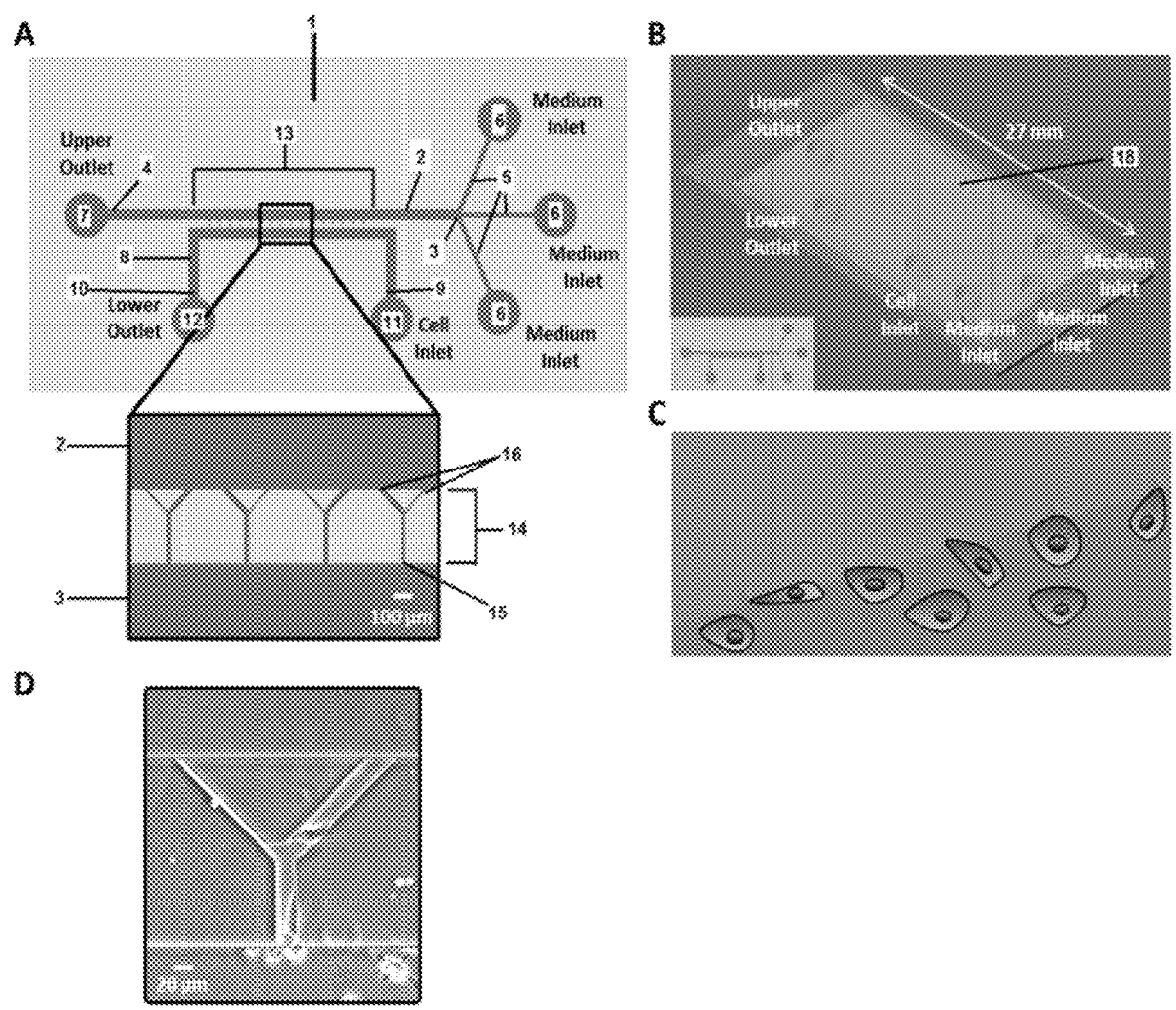
FIG. 1 illustrates an embodiment of the apparatus of the present invention. (1A) A schematic of dwice, showing overall design of an embodiment used in the methods disclosed herein. Inset shows details of Y-shaped microchannels. (1B) Schematic of completed PDMS device bonded to glass coverslip. (1C) Schematic of cells seeded at channel bases. (1D) Phase contrast image of MDA-MB-231 cells migrating in 200 μm-long Y-shaped microchannels.

The present invention describes an integrated apparatus that enables identification of migratory cells directly from a specimen. The apparatus only requires a small number of cells to perform an assay. The apparatus of the present invention includes novel topographic features which can reliably differentiate between migratory and non-migratory cell populations in a sample. Furthermore, in some embodiments, both the spontaneous and chemotactic migration of cancer cells may be measured to distinguish between subpopulations within a tumor sample. The migratory cells identified using the apparatus and methods of the present invention may be separated and further analyzed to distinguish factors promoting, metastasis within the population. Cells in the apparatus can be treated with chemotherapeutic or other agents to determine drug strategies to most strongly inhibit migration. The use of optically transparent materials in some embodiments allows a wide range of imaging techniques to be used for in siut imaging of migratory and non-migratory cells in the apparatus. The apparatus and methods of the present invention are useful for predicting the metastatic propensity of tumor cells and selecting optimal drugs for personalized therapies.

In an embodiment, the apparatus comprises a substrate in the form of a chip having a plurality of layers. In one embodiment, the chip comprises a fluid layer and a coverslip layer, which are fused together at final assembly of the apparatus. The fluid layer is composed of a plurality of channels having at least one or more inlets and outlets.

In an embodiment, the fluid layer of the apparatus of the present invention comprises at least two channels, each having at least one or more inlets which communicate with a reservoir, and each channel also having at least one or more outlets which communicate with a reservoir. The channels can have any dimension within the limits of the depth of the substrate. In some embodiments, the channels can have dimensions of about 30 μm to about 100 μm in height and about 100 μm to about 400 μm wide.

Within the fluid layer of the substrate, in some embodiments, there are at least two channels, a first channel, also termed "a medium channel" which can be Idled with any type of biological media or solvent. There is also at least a second channel, also termed "a cell channel" which can be filled with any type of biological media or solvent that contains a sample of cells to be assayed. In an embodiment, the first and second channels are disposed in proximity to each other and are parallel into at least a portion of the two channels in the fluid layer of the substrate. The first and second channels have at least one inlet portion which can be the same or have a smaller dimension than the main portion of the first and second channel. Each inlet portion is connected to the inlet end of the first and second channel and communicates with the channels. Each inlet portion is also in communication with a reservoir wherein media or fluid can be introduced into the inlet of the channel.

The first and second channels have at least one outlet portion which is the same dimension as the main portion of the first and second channel. Each outlet portion is connected to the outlet end of the first and second channel and communicates with the channels. Each outlet portion is also in communication with a reservoir wherein media or fluid can be directed to or removed from the channel.

In one or more embodiments, a novel aspect of the apparatus of the present invention is located in the migratory channel portion of the apparatus. In an embodiment, the migratory channel portion is an area where the first channel and second channel are in proximity to each other and are connected by a plurality of migratory channels having at least one inlet and at least one or more outlets. The migratory channels, in some embodiments, are bifurcated at a point distal from the inlet portion of the migratory channel. In some embodiments, the bifurcation results in two outlet portions of the migratory channel which communicate with the media channel. These channels are significantly reduced in size, for example, by approximately a factor of 10, so as to allow one cell body at a time to enter the migratory channel from the cell channel. For example, in an embodiment, the main portion of the first and second channels has a width of about 400 μm and a height of about 50 μm, whereas the migratory channels have an inlet portion which communicates with the second channel and has a width of about 20 μm and a height of about 10 μm. In some embodiments, the migratory channels can have dimensions of width of about 3 μm to about 50 μm, and a height of about 4 μm to about 15 μm. The one or more outlet portions of the migratory channels can have the same or ditierent widths than the inlet portion of the migratory channel. The bifurcation angle of the migratory channels is about 30° to 70° from the horizontal, which is defined as the long axis of the first and second channels. It is in these migratory channels that the cells in the sample are assayed for their ability to transverse the migratory channels and their speed, physical and biochemical characteristics can be measured.

Referring now to FIG. 1A which depicts an embodiment of the apparatus of the present invention, the fluid layer of the substrate is shown generally as (1) and is composed of a polydimethylsiloxane (PDMS) chip molded from a negative replica on a silicon wafer on which photolithography has been used to create a plurality of channels. A first channel (2), which has an inlet portion (3) and an outlet portion (4). The inlet portion is in communication with three inlets (5), termed "medium inlets" which are channels in the substrate that communicate between the inlet portion (3) and an inlet reservoir (6). The outlet portion (4) is in communication with an outlet reservoir (7), termed "upper outlet." On the fluid layer is also disposed a second channel (8), termed "cell channel" which has an inlet portion (9) and an outlet portion (10). The inlet portion (9) of the second channel is in communication with an inlet reservoir (11), termed "cell inlet." The outlet portion (10) of the second channel is in communcation with an outlet reservoir (12), termed "lower outlet." In some embodiments, the inlet and outlet reservoirs are punched into the substrate of the coverslip layer having a circular shape and a diameter of about 6 mm, although that is only limited by the size of the volume required and the space available on the substrate.

On the fluid layer there is a migratory channel portion 13) which is a region between the first channel (2) and second channel (3) that has a plurality of migratory channels (14) which communicate with the first and second channels. As seen on the exploded inset in FIG. 1A, the migratory channels (14) have an inlet end (15) which communicates with the second channel (3), and two or more outlet ends (16), which are in communication with the first channel (2). The two or more outlet ends (16) are the result of a bifurcation (17) of the migratory channel and a point distal from the inlet end (15) of the migratory channel. In an embodiment, there are about 16 migratory channels (14) which connect the first (2) and second (3) channels in the migratory channel portion (13) of the fluid layer.

In an alternative embodiment, there are about 240 migratory channels (14) which connect the first (2) and second (3) channels in the migratory channel portion (13) of the fluid layer.

In some embodiments, the first and second channels are between about 10 to about 50 mm in length, and have a height/depth of between about 30 to about 100 μm, and a width of about 100 to about 400 μm. In some embodiments, the inlets for the first and second channels have a length of between 2 to about 10 mm, a height/depth of between about 30 to about 100 μm, and a width of about 50 to about 400 μm. In some embodiments, the migratory channels have a length of between about 200 to 400 μm, a height/depth of between about 4 to about 15 μm, and a width between about 3 to about 50 μm.

As seen in FIG. 1B, the apparatus has a coverslip layer (18) which in whole, or in part, is made of an optically transparent substrate. Any optically substrate which is compatible with the fluid layer substrate can be used. In an embodiment, the coverslip layer is formed of glass. It will be understood by those of ordinary skill that the portion of the coverslip layer that is optically transparent will allow visualization and imaging of the cells in the apparatus in real time. The coverslip is bonded using a variety of known means. In an embodiment, the coverslip is bonded to the fluid layer via, plasma treatment of about 18 W for a sufficient time, for example, about 2 minutes.

Before use, the fluid layer channels are all treated with 20 μg/ml collagen, such as rat tail collagen type 1, for about an hour at 37° C., and then the channels are washed with PBS or similar buffer. In some embodiments, other extracellular proteins, such as fibronectin, VCAM-1, hyaluronic acid, or gelatin, are used.

The apparatus can be used for a variety of assays to detect and quantify the micromechanical, morphological, and molecular signatures of migratory and non-migratory cells in the device.

Generally, operation of the apparatus comprises a first wash of the first channel and media inlet reservoirs (6) with a medium free buffer such as DPBS. This is followed by seeding of cells of interest from a sample. Cells of interest are seeded or introduced into the cell inlet reservoir (11) of the second channel. In some embodiments, the cells are trypsinized and suspended in serum free medium at a concentration of about $1\times10^5$ to about $5\times10^6$ cells/ml. In an embodiment, the cells are suspended at a concentration of about $2\times52\times10^6$ cells/ml. About a 50 μl aliquot of the cell suspension is introduced into the cell inlet reservoir (11), and the cells are incubated a 37° C. for a time sufficient to allow the cells to seed at the base of the migratory channels (14), for example, about 2 to about 30 minutes, preferably between about 5 to about 10 minutes. In an embodiment, about 10 to 50 μl of a suitable biological medium or buffer are introduced to the lowermost medium inlet reservoir (6) to prevent convective flow of cells through the migratory channels (14). Any remaining cells in the cell inlet reservoir (11) are then removed. Cell seeding is followed by introduction of a suitable biological medium or buffer into the media channel of the apparatus via the medium inlet reservoirs (6) and the flow is in the direction of the upper outlet (FIG. 1A). A suitable biological medium or buffer is also introduced into the cell inlet reservoir (11) of the second channel. The apparatus can be manipulated to either induce a chemoattractant gradient across the migratory channels, or not to have any chemoattractant gradient. When inducing a gradient, biological medium or buffer containing the chemoattractant is introduced into the uppermost medium inlet reservoir (6), with biological medium or buffer without the chemoattractant introduced into the remaining medium inlet reservoirs (6), and into the cell inlet reservoir (11) of the second channel. This creates a chemoattractant gradient across the migratory channels (14). If no gradient is desired, the medium inlet reservoirs (6) and cell inlet reservoir (11) are filled with the same biological medium or buffer. In some embodiments, other biologically active compounds or molecules can be added to the cell suspension when the cells are introduced into the apparatus, or alter the cells have been seeded, to perform a variety of experiments.

In operation, the apparatus is placed in a temperature and $CO_2$ controlled incubator, imaging chamber or stage type device, to which is mounted an imaging system. In some embodiments, the migrating cells are imaged at 10× magnification using a phase contrast or other optical arrangement and images are taken at periodic intervals and saved on computer or other electronic storage media for up to about 16 hours. It will be understood by those of ordinary skill that the type of microscopic imaging equipment can vary and can include any known systems or apparatus which can image cells using any type of electromagnetic radiation. Imaging systems include, but are not limited to, phase contrast, brightfield, differential interference contrast, fluorescence, and confocal microscopy and in-line holography.

In accordance with one or more embodiments, the operation of the apparatus and methods of the present invention can be performed without the need of external pumps or valves, and the function is driven by gravity and the topography of the channels in the apparatus. However, it is contemplated that alternative embodiments of the invention could encompass external pumps or valves depending on the function desired, and is well within the ability of the skilled artisan.

In a preferred embodiment, the apparatus and methods of the present invention include methods for prognostic purposes in which migration of cancer cells to one of the bifbreation branches of the migration channels is associated with a diseased state. In this embodiment, migration in the device serves as a companion diagnostic with other methods of cancer diagnosis. A high migration score indicates that the specific cancer tested has a high propensity to metastasize and indicates that aggressive treatment should be undertaken.

Figure 2:
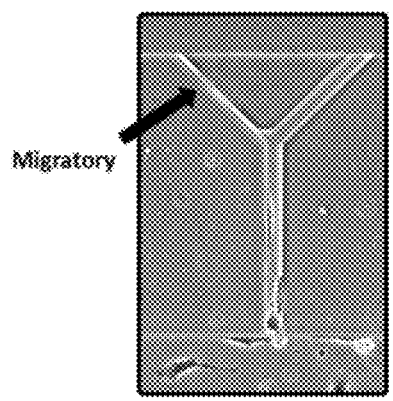
FIG. 2 illustrates the migration of migratory and non-migratory MDA-MB-231 cells within the device. (2A) Representative image of migratory cell in 3 μm-wide branch channel. (2B) Representative image of non-migratory cell within base channel of device. Migratory cells moved within the microchannels with significantly greater average speed (2C) and chemotactic index (2D). (2E) Ellipses fit to the cell outlines had major axes highly aligned with the base channel in 89% of the migratory cells but only 52% of the non-migratory cells. (2F) Migratory cells were significantly more elongated than non-migratory cells, as measured by the circularity of the cell outline. *, $p<0.05$.
Figure 2:
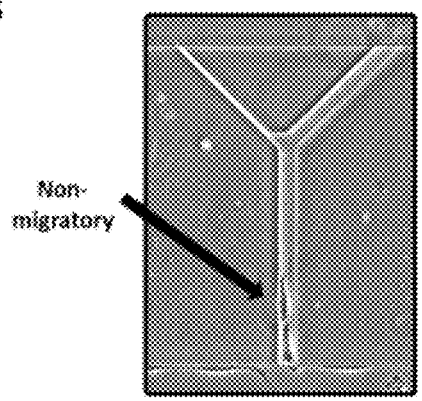
Figure 2:
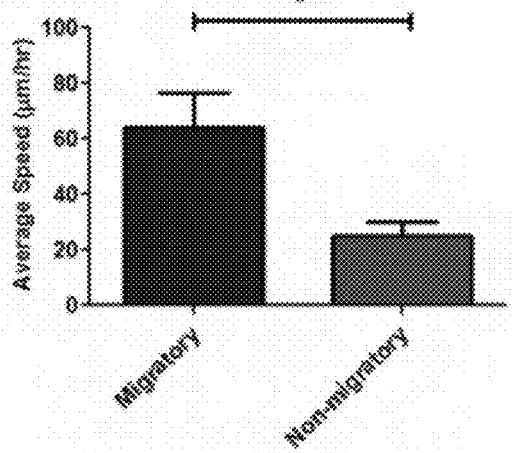
Figure 2:
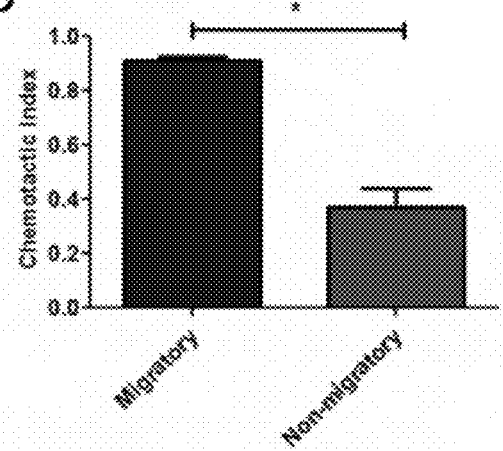
Figure 2:
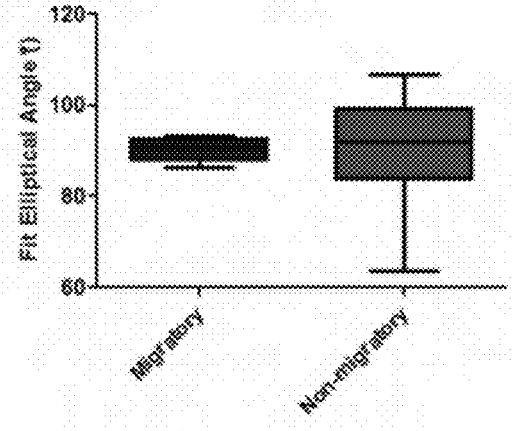
Figure 2:
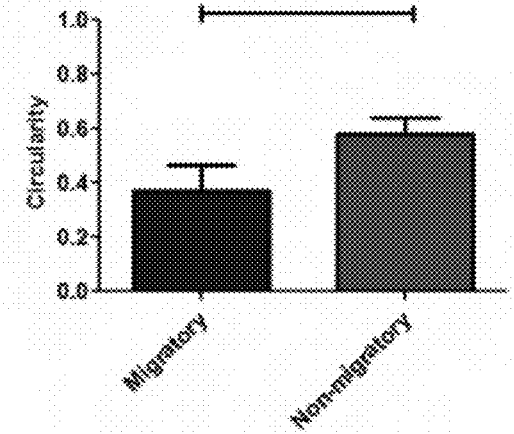

It is also contemplated that the apparatus of the present invention can be used to isolate or separate a cell or subpopulation of cells from a collection of cells in a sample. In accordance with an embodiment, cells can be separated from the device by means of trypsinization or chelation, which allows the cells to detach from the channel walls. For example, trypsin or EDTA can be introduced into all of the inlet reservoirs. The cells detach and the flow of the apparatus is such that the cells that have migrated through the migratory channels will flow through the first channel and move into the upper outlet reservoir (FIG. 2A).

In some embodiments, the migratory cells may be isolated from the apparatus and subjected to genomic or proteomic analysis. Such analysis includes, but is not limited to, analysis of gene expression levels using quantitative real-time polymerase chain reaction and of surface protein expression levels using flow cytometry.

In accordance with an embodiment of the present invention, it will be understood that the term "biological sample" or "biological fluid" includes, but is not limited to, any quantity of cells from a living or formerly living subject. Such cells include, but are not limited to, blood, bone, bone marrow, T-cells, B-cells, fibroblasts, chondrocytes, synovial macrophages, endothelial cells, tumor associated cells, and skin cells.

As used herein, the term "subject" refers to any inammal, including, but not limited to, mammals of the order Rodentia, such as mice and hamsters, and mammals of the order Logomorpha, such as rabbits. It is preferred that the mammals are from the order Carnivam, including Felines (cats) and Canines (dogs). It is more preferred that the mammals are from the order Artiodactyla, including Bovines (cows) and Swines (pigs) or of the order Perssodactyla, including Equines (horses), it is most preferred that the mammals are of the order Primates, Cebolds, or Siinoids (monkeys) or of the order Anthropoids (humans and apes). An especially preferred mammal is the human.

The solid substrate used to make the apparatus of the present invention may be any suitable material. Representative examples of substrates include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon including PDMS, carbon, metals, inorganic glasses and plastics. In a preferred embodiment, the material used in the substrate is modified silicon.

In some embodiments, the apparatus and methods used are methods of diagnosis and the migration of cells is associated with a diseased state. In one preferred embodiment, the migration of cells is associated with cancer, such as prostate cancer, melanoma, bladder cancer, breast cancer, lymphoma, ovarian cancer, lung cancer, colorectal cancer or head and neck cancer. In other preferred embodiments, migration of cells is associated with an immunological disorder; inflammation; rheumatoid arthritis; cystic fibrosis; or an infection, for example, a viral or bacterial inf ection, in other embodiments, the apparatus and methods used are methods of monitoring prognosis and the migration of cells is associated with the prognosis of a disease.

In yet another embodiment, the apparatus and methods used are for monitoring drug treatment and the migration of cells is associated with the drug treatment. In particular, the apparatus and methods used are (e.g., analysis of migration of cells) for the selection of population-oriented drug treatments and/or in prospective studies for selection of dosing, for activity monitoring andior for determining efficacy endpoints. In this embodiment, decreased migration upon application of a particular biologically active molecule indicates that that molecule effectively inhibits the movement of migratory cells.

The diagnosis can be carried out in a person with or thought to have a disease or condition. The diagnosis can also be carried out in a person thought to be at risk for a disease or condition. "A person at risk" is one that has either a genetic predisposition to have the disease or condition or is one that has been exposed to a factor that could increase his/her risk of developing the disease or condition.

Detection of cancers at an early stage is crucial for its efficient treatment. Despite advances in diagnostic technologies, many cases of cancer are not diagnosed and treated until the malignant cells have invaded the surrounding tissue or metastasized throughout the body. Although current diagnostic approaches have significantly contributed to the detection of cancer, they still present problems in sensitivity and specificity.

In accordance with one or more embodiments of the present invention, It will be understood that the types of cancer diagnosis which may be made, using the apparatus and methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having, a potential benefit or therapeutic effect. In this respect, the inventive apparatus and methods can provide any amount of any level of diagnosis, staging, screening, or other patient management, including treatment or prevention of cancer in a mammal In accordance with the inventive apparatus and methods, the terms "cancers" or "tumors" also include but are not limited to adrenal gland cancer, biliary tract cancer; bladder cancer, brain cancer, breast cancer, cervical cancer; choriocarcinatna; colon cancer; endometrial cancer; esophageal cancer; extrahepatic bile duct cancer; gastric cancer; head and neck cancer; intraepithelial neoplasms; kidney cancer; leukemia; lymphomas; liver cancer; lung cancer (e.g. small cell and non-small cell); melanoma; multiple myeloma; neuroblastomas; oral cancer; ovarian cancer; pancreas cancer; prostate cancer; rectal cancer; sarcomas; skin cancer small intestine cancer; testicular cancer; thyroid cancer; uterine cancer; urethral cancer and renal cancer, as well as other carcinomas and sarcomas.

An "active molecule" and a "biologically active molecule" are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, pmdnigs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

As used herein, biologically active molecules which can be introduced into the apparatus and used in the methods disclosed herein include, but are not limited to, dyes, including fluorescent, and NIRF dyes, enzymes, and enzyme linked dyes and markers, receptor antagonists or agonists, hormones, growth factors, autogenous bone marrow, antibiotics, antimicrobial agents, and antibodies. Non-limiting examples of biologically active agents include following: adrenergic blocking agents, anabolic agents, androgenic steroids, antacids, anti-asthmatic agents, anti-allergenic materials, anti-cholesteroleinic and anti-lipid agents, anticholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, antimalarials, anti-manic agents, anti-nauseants, anti-neoplastic agents, anti-obesity agents, anti-parkinsonian agents, antipyretic and analgesic agents, anti-spasmodic agents, antithrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, minitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

When the biologically active molecule is a dye, the molecule is detected by fluorescence imaging. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarin, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

The teen "modulate," as used herein means that in the presence of the biologically active agent or molecule, the migratory ability of the cell or subpopulation of cells is up regulated or down regulated, such that migration level, or activity is greater than or less than that observed when compared to controls. For example, the term "modulate" can mean "inhibit," but the use of the word "modulate" is not limited to this definition.

The term "inhibit" as used herein, means that that in the presence of the biologically active agent or molecule, the migratory ability of the cell or subpopulation of cells is lowered or down regulated when compared to controls.

EXAMPLES

Fabrication of an embodiment of the apparatus of the present invention: The microfluidic device consisted of "Y"-shaped inicrochannels, with a 20 µm-wide feeder channel bifurcating to 20 µm-wide or 3 µm-wide branches, arrayed between mutually perpendicular cell seeding and cell outlet channels. Microchannels were of height $H_C=10$ µm and length $L_C=200-400$ µm and were spaced 50 µm apart.

The apparatus was fhbricated using multilayer photolithography and replica molding. Photolithography masks were designed using. AutoCAD (Autodesk, McLean, VA) and produced by the Photoplot Store (Colorado Springs, CO)). The master for the device contained a negative mold of the final device and was fhbricated using SU-8 3010 positive photoresist (Microchem, Newton, MA). SU-8 3010 was spin coated (Single Wafer Spin Processor, Model WS-400A-6NPP-LITE, Laurell Technologies, North Wales, PA) on a cleaned silicon wafer (University Wafer, South Boston, MA) to create a 10 µm-thick film. The film was soft baked on a hot plate and exposed to 170 mJ/cm2 of UV light energy through the chrome-on-glass light field mask using an EVG620 mask aligner (EVG, Austria) to define the microchannels. The wafer was baked, post-exposure, to cross link the pattern before development with SU-8 developer. Follow development, a 50 µm-thick SU-8 3025 film was spun onto the wafer and soft baked. A mask defining the medium feed lines was aligned with the channels, and the photoresist was exposed to 250 mJ/cm2 of energy. The final master was developed, hard baked, and passivated with a fluorinated silane [(tridecafluoro-1,1,1,2-tetrahydrooctyl)-1-trichlorosilane]0 (Pfaltz & Bauer, Waterbury, CT) overnight in a vacuum desiccator.

Completed devices were molded from the SU-8 masters by pouring polydimethylsiloxane (PDMS) (Sylgard® 184 Silicone Elastomer Kit, Dow Corning, Midland, MI) at a 10:1 ratio of prepolymercrosslinker over the master, degassing, and curing at 85° C. for 2 hours. Devices were diced, and 6-mm inlet and outlet ports were punched in the PDMS fluid layer. The devices and glass coverslips were cleaned with ethanol and DI water and plasma treated for 2 minutes at 18 W (Harrick PDC-32G, Harrick Plasma, Ithaca, NY). The device was bonded to the glass slide and coated with 20 µg/ml rat tail collagen type 1 (BD, Franklin Lakes, NJ USA) for 1 hour at 37° C. Following coating, the channels were washed with DPBS to prepare for cell seeding.

Description of an embodiment of the apparatus used in the examples of the present invention. The apparatus, termed a "Microchannel Migration Device," comprises a plurality of Y-shaped microchannels arrayed between cell seeding (second channel) and medium (first channel) lines (FIG. 1A). The microchannels were designed such that 20 µm base channels bifurcated to 20 µm and 3 µm branch channels at a 45° or 65° (from the horizontal) angle (inset, FIG. 1A). With this device design, experiments can be carried out with or without a chemoattractant gradient. If no gradient is desired, growth medium is placed in all four inlet wells, and the topography of the channels is the only driver of migration. When medium containing a chemoattractant is placed in the uppermost medium inlet well and medium without chemoattractant is placed in the cell inlet and bottom two medium inlet wells, a gradient is formed within the microchannels to induce migration.

The particular embodiment of the device was formed by bonding a PDMS mold containing the rnicrochannels and medium channels to a glass coverslip (FIG. 1B). Cells were seeded at the bases of the microchannels following gravity-driven flow of suspended cells from the cell inlet well (shown schematically in FIG. 1C). Medium was placed in all inlet wells following cell seeding. Importantly, cell seeding and migration were carried out without the need for external pumps or valves, and all flow was driven by gravity. Seeded cells migrated through the channels over the course of the experiment (FIG. 1D).

Cell seeding and live cell migration experiments: Cells were grown to continency, trypsinized, and resuspended in serum-free medium at $2 \times 10^6$ cells/ml. 50 µl of cell suspension was added to the cell inlet well. Cells were incubated in the device for 5-10 minutes at 37° C. to allow initial cell seeding at the base of "Y" channels. The cell suspension was then removed from the cell inlet port. The device was washed with DPBS before the addition of medium to the inlet ports of the device. In select experiments, PI3K activity was inhibited by the addition of 10 µM LY294002 in the medium through the entire course of migration. The migration chamber was moved to a temperature- and $CO_2$-controlled stage-top live cell incubator (Okolab, Italy) mounted on the motorized stage of an inverted Nikon Eclipse Ti microscope (Nikon, Tokyo, Japan) with automated controls (NIS-Elements, Nikon). Migrating cells were imaged with a 10×-magnification phase contrast objective every 10 minutes for up to 16 hours.

Analysis of Cell Migration: Video tiles were exported to ImageJ for analysis. All cells that entered the channel were tracked while fully inside the channel and before reaching either end of the channel using the lmageJ MTrackJ plugin at 10 minute intervals. Cells were also dynamically traced with the imageJ polygon ROI capability at 30 minute intervals. Dividing cells were not tracked.

Cell position data were used to calculate cell speed over each 10 minute interval, and these speeds were averaged to get an overall average speed for each cell. Additionally, the chemotactic index, defined as the cell displacement divided by the total distance travelled by the cell, was calculated. Cell shape data were used to calculate cell circularity and fit elliptical angle using the Measure function in ImageJ Statistical significance was assessed with non-paired Student's t-test.

Cells were further defined as migratory or non-migratory. Migratory cells were defined as those cells which reached the bifurcation in the Y-shaped microchannel; all other cells were defined as non-migratory. Migratory cells were then classified as contact guided or not contact guided. Cells were defined as contact guided if they continued to the branch channel on the side of the base channel on which they were migrating when the bifurcation was reached. Cells that switched walls in the bifurcation region were classified as not contact guided.

Isolation of Migratory Cells: Cells that had migrated through and exited the channels were washed with a dictator (versene) prior to the addition of 0.25% trypsin to all inlet wells of the device. Hydrodynamic resistance to flow in the narrow microchannels prevented the backflow of cells that had migrated through the microchannels back into the microchannels. Detached cells flowed to the upper outlet well, were collected in culture medium, and were plated in 96-well plates for expansion. Expanded cells were analyzed for the presence of tumor stein cell markers (for example, CD44 or CD271).

Alternatively, ~300 migratory cells were collected, suspended in 75 µl of DPBS, mixed with 75 µl of Matrigel, and injected to the mammary fat pad of an immanodificient mouse. An equal number of control cells that had not migrated through the microchannels were collected and injected in an identical manner. Mice were sacrificed 8 weeks post-injection, and the lungs were histologically analyzed to detect metastases.

Example 1

Bifurcating Channels Allow Identification of Migratory Cells: Cell tracking of all MDA-MB-231 cells within the channels revealed two distinct subpopulations: migratory and non-migratory cells (FIGS. 2A,B). 22±3% of human metastatic MDA-MB-231 breast cancer cells were migratory. Interestingly, this subpopulation correlates with the of MDA-MB-231 (28%) bearing the CD44+/CD24− molecular signature[5] that is used to define breast cancer stem cells. Migratory cells, defined as those cells reaching the branch channels, migrated more than twice as fast as non-migratory cells (FIG. 2C). Migrartory cells were also significantly more directional. The chemotactic index of migratory cells increased to 0.91 in comparison to a chemotactic index of 0.37 for nomnigratory cells.

Figure 3:
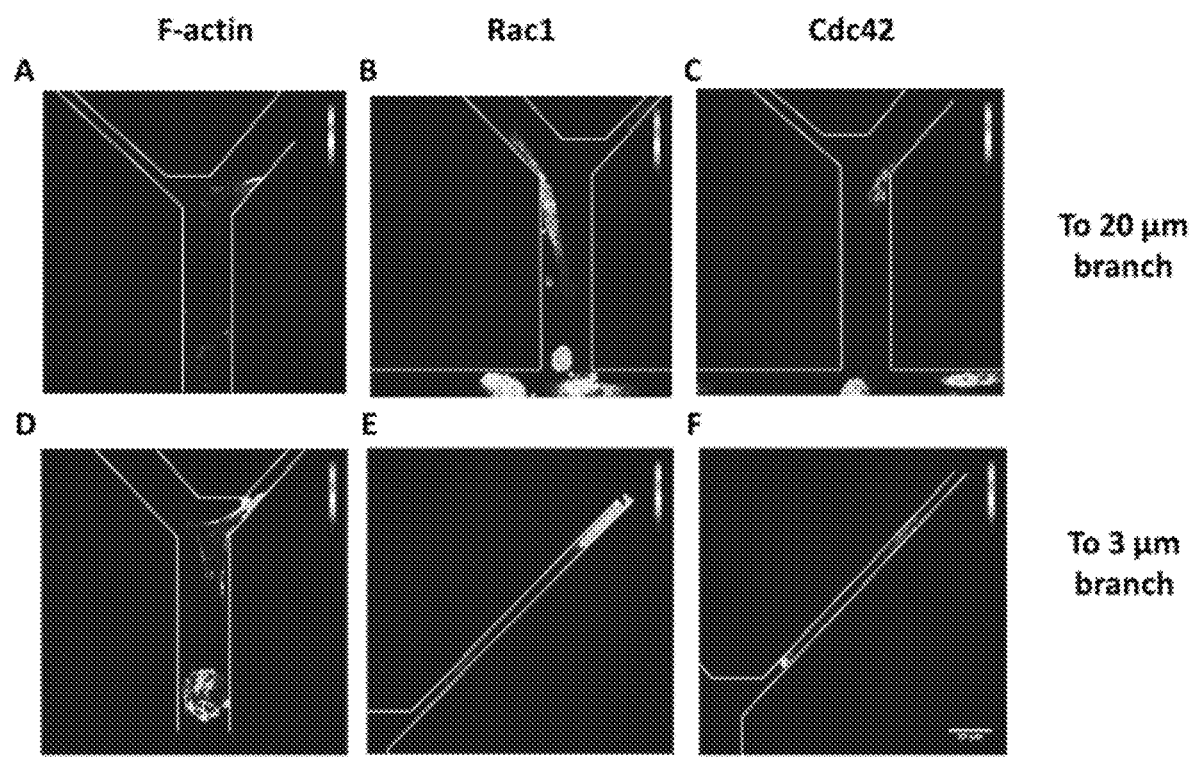
FIG. 3 shows fluorescent on-chip imaging of F-actin and Rho GIPases. MDA-MB-231 ells within the microchannels were fixed and stained for (3 A,D) F-actin, (3 B,E) Rac1, or (3 C,F) Cdc42. Panels 3A-C show cells entering the 20 μm-wide branch channel. Panels 3D-F show cells entering or migrating within the 3 μm-wide branch channel. Non-migratory cells are shown at the 20 μm-wide channel bases in panels B and D (arrows).

Analysis of cell shape indicated that migratory cells were aligned with and elongated along the channel wall. The fit elliptical angle of a cell perfectly aligned along the wall was 90°. Although both migratory and non-migratory cells had an average fit elliptical angle of 90°, 89% of migratory cells had fit elliptical angles within 10° of 90°, while only 52% of non-migratory cells showed this high degree of alignment (FIG. 2E). This directed migration was confirmed by analysis of migration in the base channel. In that region of the microchannel, migratory cells changed direction an average of 0.6 times, while non-migratory cells averaged 5.6 direction changes. Circularity, a shape factor that decreases as shapes become less circular, was also significantly different between migratory and non-migratory cells. Migratory cells were significantly more elongated as they migrated, with a circularity of 0.37. Non-migratory cells had an average circularity of 0.58 (FIG. 2F). Additionally, the apparatus of the present invention was used for analysis of cytoskelctal components and intracellular signals via fluorescence microscopy (FIG. 3). This was possible because the device was constructed of transparent materials. Migratory cells showed increased localization of F-actin to the cell leading edge (FIG. 3A, D). Actin localization was not seen in non-migratory cells (rounded cell at base of channel, FIG. 3D). Similarly, the Rho CaPases Rac1 and Cdc42 were polarized in migratory cells, particularly when these cells reached the 3 µm-wide branch channel (FIG. 3B,C,E,F). Non-migratory cells did not exhibit this polarization (for example, cell at channel base in FIG. 3B).

Example 2

Figure 4:
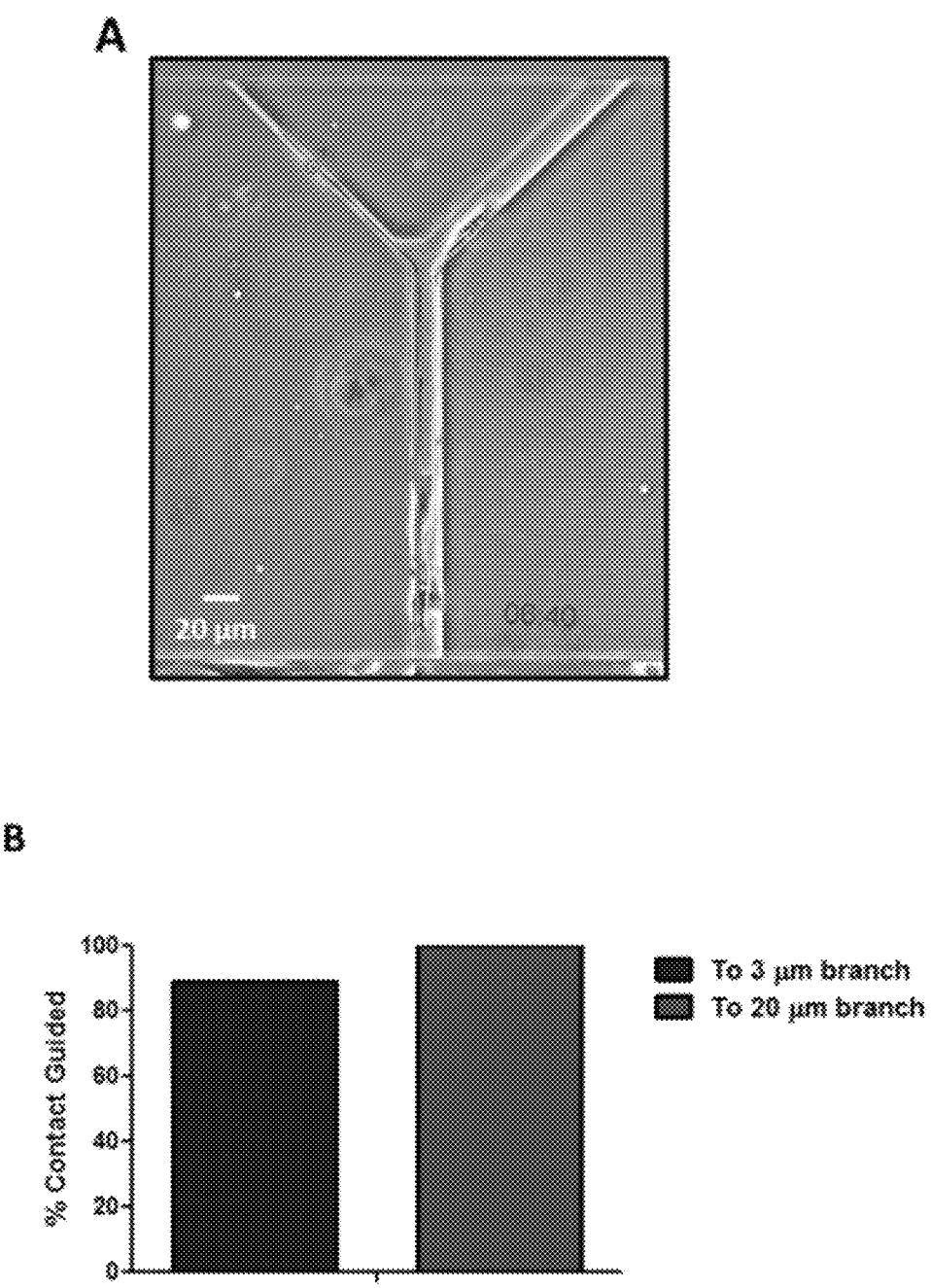
FIG. 4 depicts how migratory MDA-MB-231 cells are contact guided at the microchannel bifurcation. (4A) Representative cell tracks of migratory cells. Cells migrate predominantly up one channel wall and continue to follow that wall at the bifurcation as they enter a branch channel. (4B) Percentage of migratory cells that were contact guided to the 3 μm-wide and 20 μm-wide branches.

Contact Guidance Overcomes Steric Hindrance for Migratory Cells: Of those cells that were migratory, the vast majority moved preferentially along one wall of the feeder channels and remaining polarized, with a significantly lower number of changes in direction compared to non-migratory cells. Representative cell tracks illustrating this trend are shown in FIG. 4A. Interestingly, migration direction at the bifurcation was not dependent on the width of the resultant branch, even though entering the 3 µm-wide branch required significant deformation of the cell body. Instead, cells continued to be polarized and moved readily into the "branch" channel, regardless of the branch channel width (FIG. 4B). Thus, contact guidance dominated steric hindrance at these channel widths for migratory cells and was likely the driver of directed migration for this subpopulation.

Example 3

PI3K Inhibition Promotes Spontaneous Migration of MDA-MB-231 Cells: There is evidence that PI3K signaling is required to stabilize nascent protrusions. New protrusions away from the wall along which a cell is migrating would discourage contact guidance. Therefore, it was investigated whether inhibiting PI3K could promote contact guidance in 200 µm-long niicrochannels.

Figure 5:
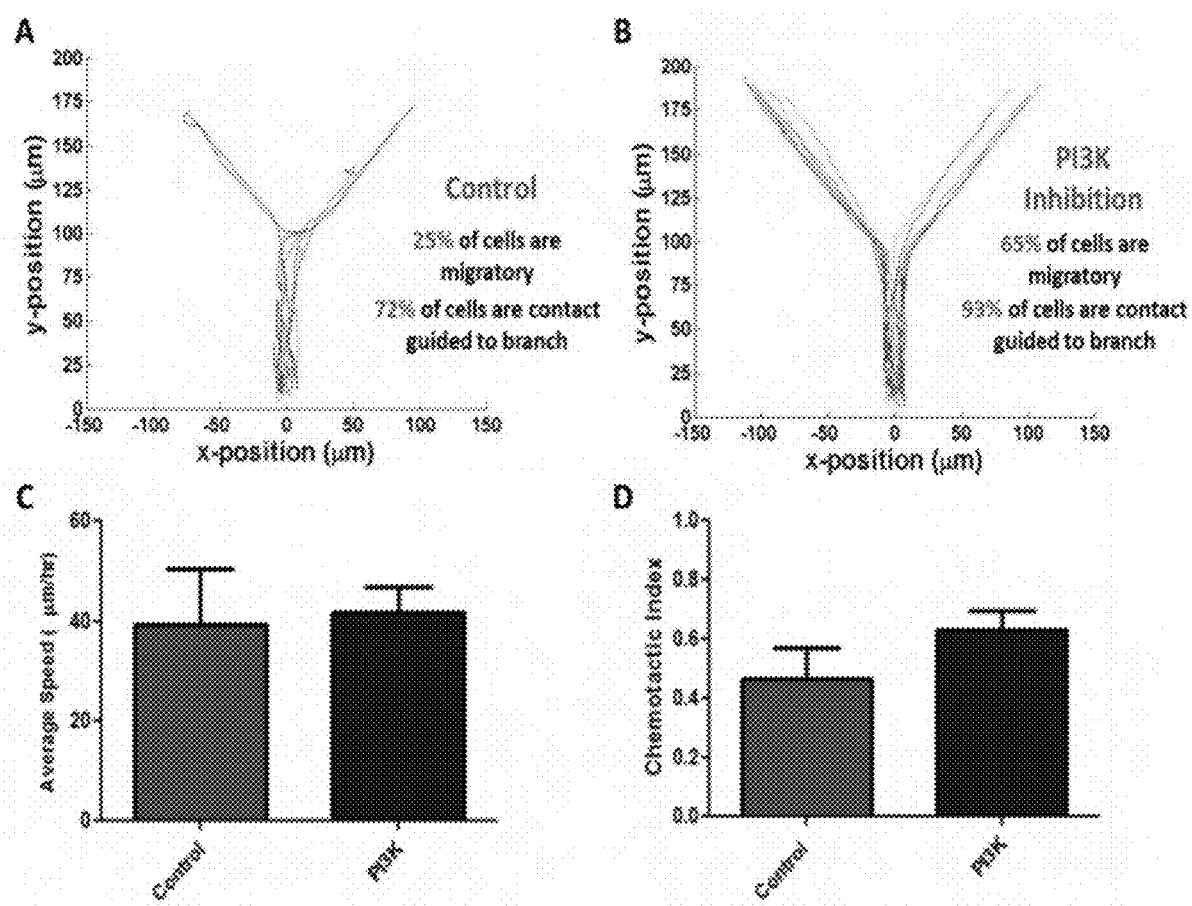
FIG. 5 illustrates that PI3K inhibition promotes MDA-MB-231 cell migration and contact guidance within the microchannels. Representative tracks of (5A) control and (5B) PI3X inhibited cells migrating within 200 μm-long microhcannels. PI3K inhibition with 10 μM LY294002 increased the percentage of cells that were migratory and that were contact guided. (5C) The average speed of control and LY294002-treated cells was the same. (5D) The chemotactic index of LY294002-treated cells was greater than that of control cells.

Inhibition of PI3K signaling using the PI3K inhibitor LY294002 increased the migratory cell population in 200 μm-long microchannels from 25% to 65% and the ratio of contact guided cells from 66% to 93% (FIG. 5A,B). PI3K inhibition did not impact overall cell speed, as control and LY294002-treated cells moved at the same average speed (FIG. 5C). However, cells in which PI3K signaling was inhibited moved with greater directionality, as indicated by the higher chemotactic index for these cells vs. control cells (FIG. 5D). This result is consistent with the expected inhibition of nascent protrusions upon LY294002 treatment, as new protrusions would be required for the cell to change direction.

Example 4

Device Design Allows isolation of Migratory Cells: Further characterization of migratory and non-migratory cells will provide important information on the nature of these cell populations. For example, we wish to characterize whether migratory cells show stem-like characteristics, retain high migratory potential over several generations, or display differential gene expression in comparison to non-migratory cells. To answer these questions, it will be necessary to isolate migratory cells from the device.

Figure 6:
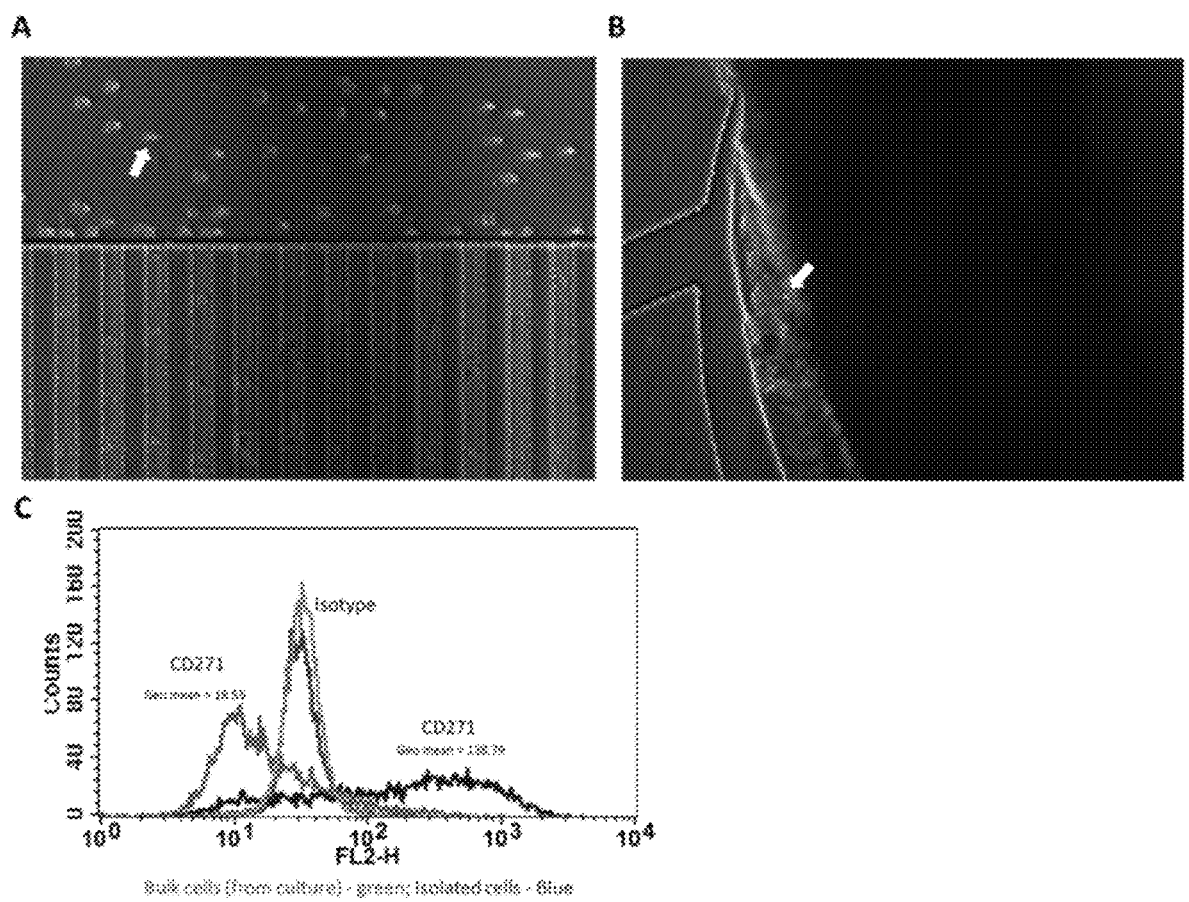
FIG. 6 depicts the extraction of migratory A375 cells from a microchannel cell migration device of the present invention. (6A) Trypsinized cells flowed in the upper medium line without entering the microchannels. Arrow indicates cell that has been completely detached from the device. (6B) Detached cells flowed to the upper medium outlet well. Arrow indicates cell entering the well. (C) Extracted A375 cells were expanded using standard cell culture techniques for 20 days and assayed for surface protein expression levels of the cancer stem cell marker CD271 using flow cytometry. A375 cells that had migrated through the device and been expanded (blue) exhibited higher surface protein expression levels of CD271 than the bulk A375 cell population (green).

Proof-of-concept experiments were performed to isolate migratory cells. A375 cells migrated through straight microchatmels toward a chemotactic cue. Trypsin was added to all inlet wells of the device and caused the migratory cells to become detached and flow to the upper medium outlet well (FIG. 6A). Resistance to flow through the narrow microchannels prevented detached cells from flowing hack into the mierochannels. Migratory cells were collected in the upper medium outlet well (FIG. 6B) and plated in 96-well plates for expansion. Expanded cells were analyzed for expression of the cancer stem cell marker CD271 using flow cytometry. Migratory A375 cells displayed increased expression of this marker compared to cell populations from which the migratory subpopulation had not been extracted (FIG. 6C).

Example 5

Figure 7:
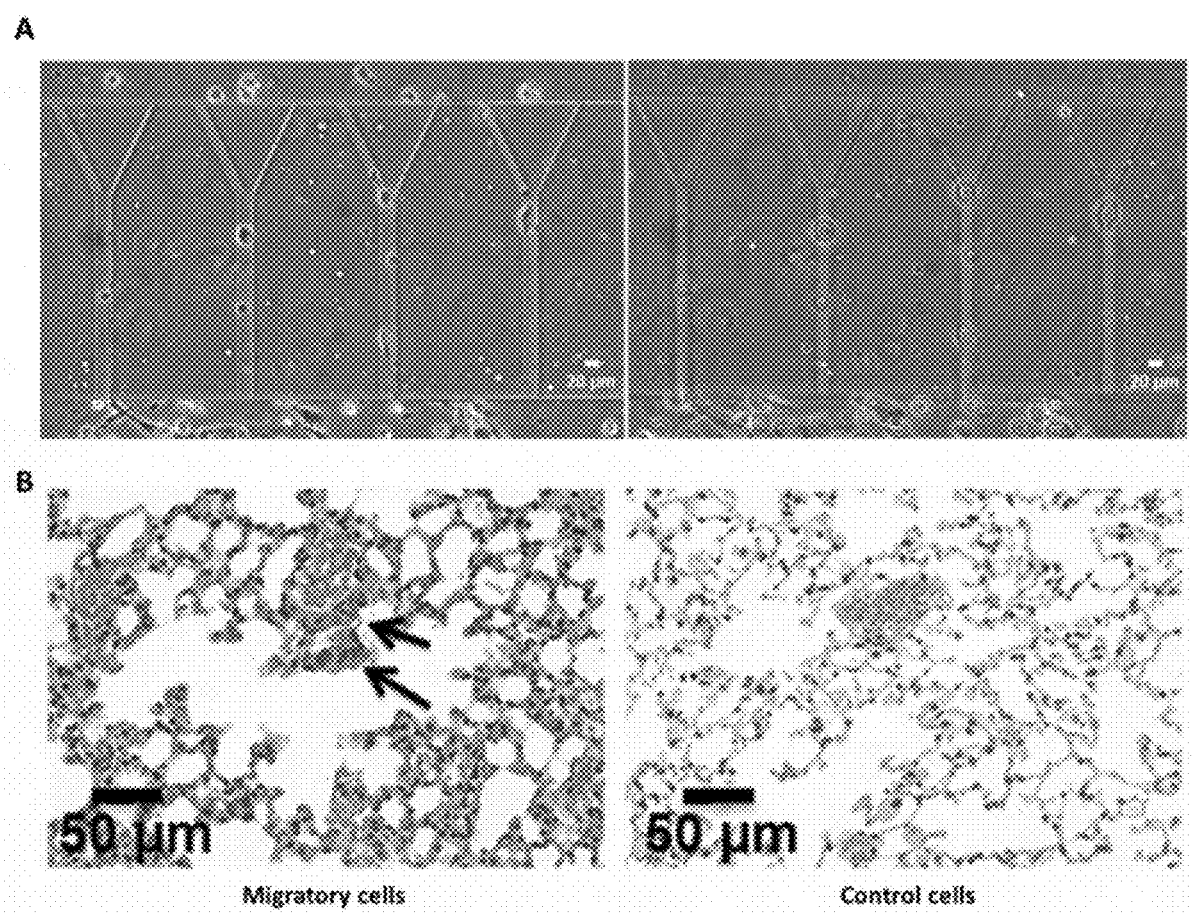
FIG. 7 depicts the isolation of migration MDA-MB-231 cells from a migration device of the present invention. (7A) Migratory cells that exited the microchannels are shown prior to (left panel) and following (right panel) extraction from the device. Note that the position of the nonmigratory cells and cells seeded at the entrances to the channels is the same before and after extraction of migratory cells. (7B) Orthotopic injection of migratory cells but not control, cells to the mammary fat pad of immodeficient mice resulted in the formation of metastases (arrows).

Migratory cells are more likely to cause metastasis upon orthotopic injection in immunodeficient mice: MDA-MB-231 cells migrated through the device in the absence of a chemotactic cue. Trypsin was added to the all medium inlet wells of the device and caused the migratory cells to become detached and flow to the upper medium outlet well (FIG. 7A). Resistance to flow through the narrow microchannels prevented detached cells from flowing back into the microchannels (FIG. 7A; compare cell positions in micmchannels before and after removal of migratory cells). Approximately 300 migratory cells were collected in the upper medium outlet well. Trypsin was then added to the cell inlet well. Cells that had not entered the channels flowed to the lower outlet well and were collected. Approximately 300 of these control cells were collected. Migratory or control cells were suspended in 75 μl DPBS, mixed with 75 μl Matrigel, and injected to the mammary fat pad of immunodeficient mice. Mice were sacrificed at 8 weeks post-injection. Histological analysis of the lungs of these mice revealed that migratory cells caused lung metastasis, whereas control cells did not (FIG. 7B; arrows indicate metastases).

Example 6

Observations using metastatic MDA-MB-231 breast cancer cells were generalized. A panel of cell lines was assayed in devices containing 400 μm-long Y-shaped migration channels (FIG. 8). None of the non-tumorigenic MCF10A breast epithelial cells or non metastatic MCF-7 breast cancer cells assayed were found to be migratory. Similarly, only 1±1% of non-metastatic MDA-MB-468 breast cancer cells were migratory. Conversely, subpopulations of motile cells were fund in metastatic K-Ras-overexpressing/obscurin-knockdown MCF10A cells (20%), metastatic Bt-549 breast cancer cells (32±8%), metastatic MDA-MB-436 breast cancer cells (13±7%), metastastic MDA-MB-231 breast cancer cells (22±3%), metastatic Hs578t breast cancer cells (20±7%), and metastatic A375 melanoma cells (38±7%). The 38±7% of migratory human A375 melanoma cells closely matches the % of A375 cells expressing the cancer stem cell marker CD271.

Example 7

Triple negative breast cancer cells display divergent responses to pharmaceutical agents: A panel of triple-negative breast cancer (TNBC) cell lines were assayed in devices containing 400 μm-long Y-shaped migration channels in the presence or absence of the PI3K inhibitor LY294002 (10 μM) (FIG. 9). PI3K inhibition did not affect the percentage of migratory cells measured for MDA-MB-436 (13±17% migratory for control vs. 1817% for treated) cells or Hs578t (20±7% migratory for control vs. 15±2% migratory for treated) cells. Pl3K inhibition increased migration of MDA-MB-231 (22±3% for control vs. 34±8% for treated) cells. In contrast, PI3K inhibition reduced the migration of Bt549 (32±8% for control vs. 19±1% for treated) cells.

Example 8

Figure 10:
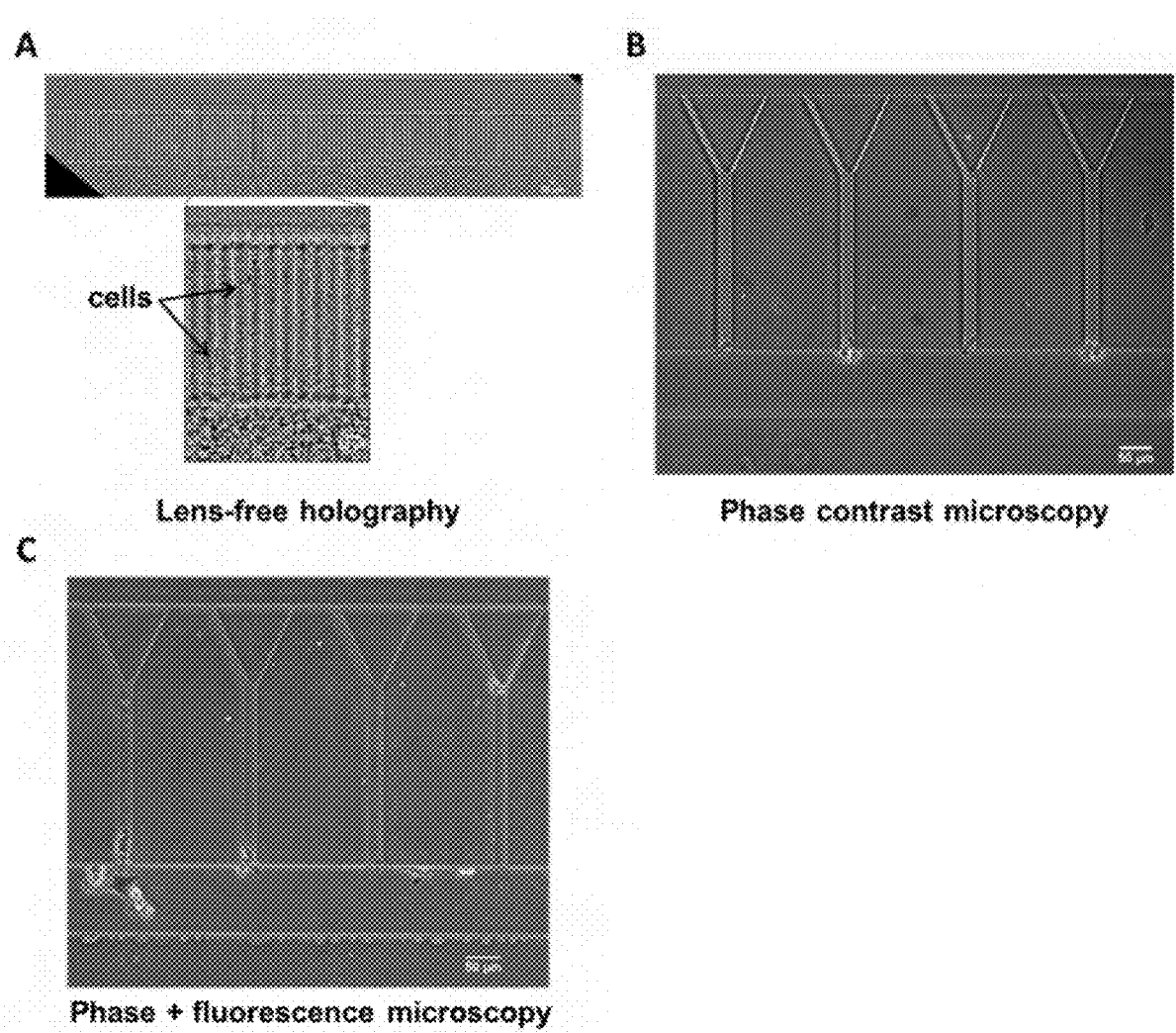
FIG. 10 depicts a representative sample of imaging techniques that can be used to assess migration in the present invention. (10A) Lens-free holography enables a wide field of view to be captured in a single image. Inset shows digitally zoomed image, with cells clearly visible in migration channels. (10B) Phase contrast microscopy (10× objective) image of migration channels with cells seeded at channel entrances. (10C) Combined phase contrast and fluorescence microscopy of cells within migration channels. A subset of cells was tagged with a fluorescent marker and appears green in the image.

Metastatic propensity assay is amenable to a wide range of imaging techniques: Numerous techniques were used to image an embodiment of the invention in which a PDMS fluidic layer is bonded to a glass coverslip layer. Cells were imaged using lens-free holography (FIG. 10A), which has an approximately 5 mm×5 mm field of view. Cells were clearly visible in the channels upon digitally zooming in (inset, FIG. 10A), Additionally, cells in the device were imaged using phase contrast microscopy (FIG. 10B) and a combination of phase contrast and fluorescence microscopy (FIG. 10C; a subset of cells was tagged with a fluorescent marker and appears green in the image).

All references, including publications, patent applications, and patents, cited herein are hereby incorporated by rekrence to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can he performed in any suitable order unless otherwise indicated herein or otherwise clearly contradicted by context. The use of any and all examples, or exemplary language (e.g., "such as") provided herein, is Intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the Inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus for analysis of cellular motility in a sample comprising:
   a chip having a fluid layer having at least first and second channels, the first and second channels each having a respective inlet end and a respective outlet end,
   wherein the first channel comprises:
      one or more inlets, each inlet of the one or more inlets having a reservoir in fluid communication with the inlet end of the first channel; and
      one or more outlets, each outlet of the one or more outlets having a reservoir in fluid communication with the outlet end of the first channel,
   wherein the second channel comprises:
      an inlet having a reservoir in fluid communication with the inlet end of the second channel; and
      an outlet having a reservoir in fluid communication with the outlet end of the second channel,
   wherein the first and second channels of the fluid layer are in communication with each other through at least one migration channel, wherein a first migration channel of the at least one migration channel comprises:
      a single inlet end in fluid communication with the second channel of the fluid layer;
      first and second outlet ends in fluid communication with the first channel of the fluid layer;
      a first body portion extending from the single inlet end toward the first and second outlet ends; and
      first and second branch portions extending, respectively, from the first body portion to the first and second outlet ends,
   wherein the first body portion of the first migration channel and the first and second branch portions of the first migration channel are connected to one another at a bifurcation of the first migration channel, and
   wherein the first and second branch portions of the first migration channel have respective widths, wherein the width of the first branch portion of the first migration channel is different than the width of the second branch portion of the first migration channel.

2. The apparatus of claim 1, wherein the first body portion of the first migration channel and the first and second channels have respective widths, and wherein the width of the first body portion of the first migration channel is smaller than the widths of the first and second channels.

3. The apparatus of claim 1, further comprising a coverslip layer comprising a transparent substrate, wherein the coverslip layer is configured for bonding to the fluid layer to form a liquid seal over a top of the fluid layer.

4. The apparatus of claim 1, wherein the chip comprises polydimethylsiloxane (PDMS).

5. The apparatus of claim 1, wherein the first and second channels have respective heights of about 30 µm to about 100 µm and respective widths of about 100 µm to about 400 µm.

6. The apparatus of claim 1, wherein the one or more inlets of the first channel comprise a plurality of inlets, each inlet of the plurality of inlets having a reservoir in fluid communication with the inlet end of the first channel.

7. The apparatus of claim 1, wherein the one or more outlets of the first channel consists of one outlet having a reservoir in fluid communication with the outlet end of the first channel.

8. The apparatus of claim 6, wherein the one or more outlets of the first channel consist of one outlet having a reservoir in fluid communication with the outlet end of the first channel.

9. The apparatus of claim 1, wherein the at least one migration channel comprises a plurality of migration channels, and wherein each migration channel of the plurality of migration channels comprises:
   a single inlet end in fluid communication with the second channel of the fluid layer;
   first and second outlet ends in fluid communication with the first channel of the fluid layer;
   a first body portion extending from the single inlet end toward the first and second outlet ends; and
   first and second branch portions extending, respectively, from the first body portion to the first and second outlet ends,
   wherein the first and second branch portions of each migration channel of the plurality of migration channels have respective widths, wherein the width of the first branch portion of each respective migration channel of the plurality of migration channels is different than the width of the second branch portion of the respective migration channel, and
   wherein the plurality of migration channels are Y-shaped and are adjacent to each other.

10. The apparatus of claim 1, wherein a portion of the second channel is parallel to a portion of the first channel.

11. The apparatus of claim 1, wherein the first channel has a main portion that extends between the inlet and outlet ends of the first channel, wherein the main portion and the one or more outlets of the first channel have the same cross-sectional dimensions.

12. The apparatus of claim 11, wherein the second channel has a main portion that extends between the inlet and outlet ends of the second channel, wherein the main portion and the outlet of the second channel have the same cross-sectional dimensions.

13. The apparatus of claim 1, wherein the first migration channel has a width of about 3 µm to about 50 µm and a height of about 4 µm to about 15 µm.

14. The apparatus of claim 9, wherein each migration channel of the plurality of migration channels has a width of about 3 µm to about 50 µm and a height of about 4 µm to about 15 µm.

15. The apparatus of claim 5, wherein the first migration channel has a width of about 3 µm to about 50 µm and a height of about 4 µm to about 15 µm.

16. The apparatus of claim 15, wherein the first body portion of the first migration channel has a width that is the same as a width of one branch portion of the first and second branch portions of the first migration channel.

17. The apparatus of claim 15, wherein the first body portion of the first migration channel has a width that is the different than respective widths of the first and second branch portions of the first migration channel.

18. The apparatus of claim 5, wherein each migration channel of the plurality of migration channels has a width of about 3 μm to about 50 μm and a height of about 4 μm to about 15 μm.

19. The apparatus of claim 5, wherein the first channel has a main portion that extends between the inlet and outlet ends of the first channel, wherein the main portion of the first channel has a length of about 10 mm to about 50 mm, wherein each inlet of the one or more inlets of the first channel has a length of about 2 mm to about 10 mm and wherein each migratory channel of the plurality of migratory channels has a length of about 200 μm to about 400 μm.

20. The apparatus of claim 19, wherein the second channel has a main portion that extends between the inlet and outlet ends of the second channel, wherein the main portion of the second channel has a length of about 10 mm to about 50 mm, wherein the inlet of the second channel has a length of about 2 mm to about 10 mm, and wherein each migratory channel of the plurality of migratory channels has a length of about 200 μm to about 400 μm.

* * * * *